United States Patent [19]

Booth et al.

[11] 3,957,990

[45] May 18, 1976

[54] OXIME CARBAMATES

[75] Inventors: David L. Booth; Richard M. Rodebaugh, both of Crystal Lake, Ill.

[73] Assignee: Morton-Norwich Products, Inc., Chicago, Ill.

[22] Filed: Mar. 5, 1975

[21] Appl. No.: 555,416

[52] U.S. Cl. ............................ 424/250; 260/250 BN
[51] Int. Cl.² .................. C07D 241/08; A01N 9/22
[58] Field of Search .............. 260/250 BN; 424/250

[56] References Cited
UNITED STATES PATENTS

| | | |
|---|---|---|
| 3,493,574 | 2/1970 | Baranyouits et al. ............ 424/251 X |
| 3,535,319 | 10/1970 | Bicking et al. ................. 260/250 BM |
| 3,577,543 | 5/1971 | Baranyouits et al. ............ 424/251 X |
| 3,895,046 | 7/1975 | Boroschewski et al. ........... 71/100 X |

*Primary Examiner*—Alton D. Rollins
*Assistant Examiner*—D. B. Springer
*Attorney, Agent, or Firm*—Jack Axelrood

[57] ABSTRACT

Novel oxime-carbamates of the formula wherein
$R_1$ is $-CH_3$, $-CH(CH_3)_2$, $-CH\underset{CH_2}{\overset{CH_2}{\diagup\diagdown}}$, $-C(CH_3)_3$, or $-C_6H_5$;
$R_2$ is $-H$ or $-CH_3$;
$R_3$ is $-CH_3$, $-CH_2CH_3$, $-(CH_2)_2CH_3$, $-(CH_2)_3CH_3$, $-CH_2CH_2Cl$ or $-C_6H_5$;
$R_4$ is $-H$, $-CH_3$, $-CH_2CH_3$, $-(CH_2)_2CH_3$, $-CH(CH_3)_2$, $-(CH_2)_3CH_3$, $-CH_2CH=CH_2$, $-CH_2C\equiv CH$, $-C_6H_5$, $-CH_2\underset{Cl}{\overset{|}{C}}H-CH_2Cl$, $-CH_2\underset{Cl}{\overset{|}{C}}=CHCl$, $-CH(OH)CCl_3$, $-CH_2CH_2X_1$, where $X_1$ is $-Cl$, $-Br$, $-NH_2$, $-OH$, $-OCOCH_3$, $-OCOCH_2Cl$, or $-OCONHCH_3$;
$R_5$ and $R_6$ are each $-H$ or $-CH_3$, with the proviso that when $R_5$ and $R_6$ are both $CH_3$ then both $CH_3$ groups may be on either the same carbon atom or on different carbon atoms;
$R_7$ is H, $-CH_3$ or $-CH_2C_6H_5$;
$X_2$ is $-Cl$, $-Br$ or $-I$; and
$n$ is 0 or 1, with the proviso that when $n$ is 1 then N bears a + charge and $X_2$ bears a − charge.

These compounds are useful as insecticides and acaricides.

106 Claims, No Drawings

OXIME CARBAMATES

BACKGROUND OF THE INVENTION

1. Field of the Invention

The present invention relates to novel oxime-carbonates and their use as insecticides and acaricides.

2. Description of the Prior Art

A number of carbamates are known to exhibit insecticidal properties. Included among these are the following currently available in commerce:

| Compound | U.S. Patent No. | Trademark |
|---|---|---|

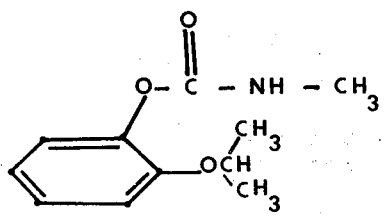

2-Isopropoxyphenyl N-Methylcarbamate 　　　3,111,539　　　BAYGON

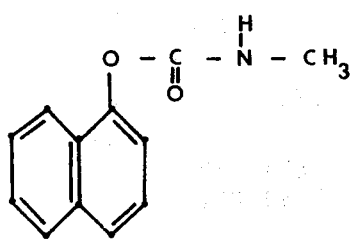

1-Naphthyl Methylcarbamate 　　　2,903,478　　　SEVIN

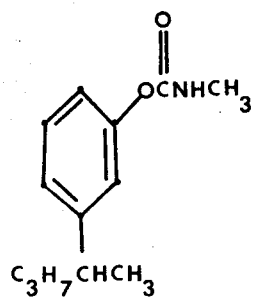

m-(1-Methylbutyl)-Phenyl Methylcarbamate

Plus

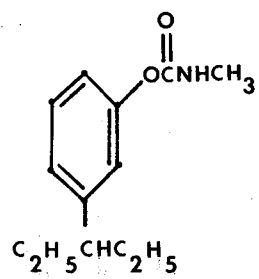

m-(1-Ethylpropyl)-Phenyl Methylcarbamate 　　　3,062,864　　　BUX TEN
　　　　　　　　　　　　　　　　　　　　　　　　3,062,867

| Compound | U.S. Patent No. | Trademark |
|---|---|---|

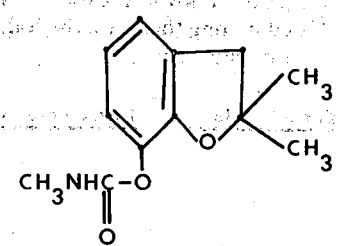

2,3-Dihydro-2,2-dimethyl-  
7-Benzofuranyl Methylcarbamate     3,474,170  
    3,474,171     FURADAN

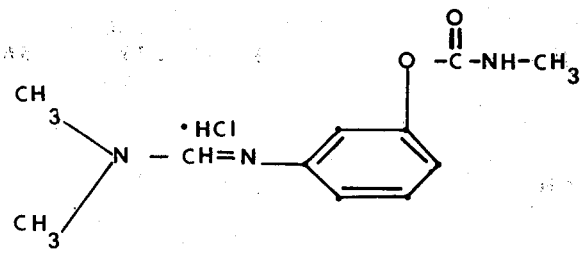

m[[(Dimethylamino)methylene]-amino]     3,336,186  
Phenyl Methylcarbamate Hydrochloride     3,542,853     CARZOL

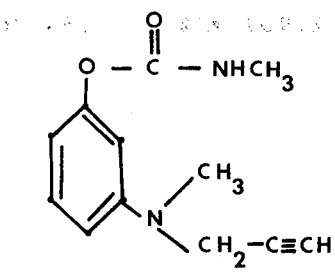

O-(Methyl-2-propinylamino)  
Phenyl N-Methylcarbamate     CGA-13608

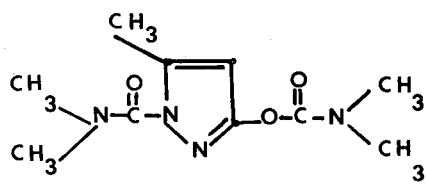

2-Dimethylcarbamyl-3-methyl-  
5-Pyrazolyl Dimethylcarbamate     DIMETILAN

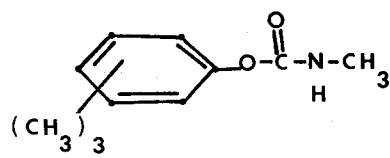

Mixture of about 20% 2,3,5-Trimethyl-  
phenyl Methylcarbamate; and 80% 3,4,5-  
Trimethylphenyl Methylcarbamate     3,130,122     LANDRIN

| Compound | U.S. Patent No. | Trademark |
|---|---|---|
| 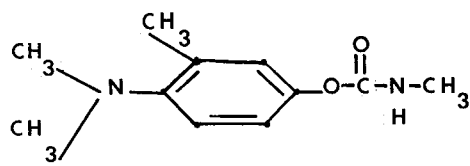<br>4-(Dimethylamino)m-tolyl Methylcarbamate | 3,134,806 | MATACIL |
| 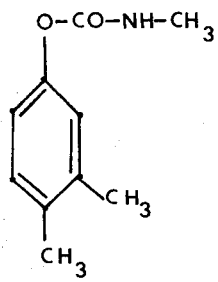<br>3,4-Dimethylphenyl-N-Methylcarbamate | | MEOBAL |
| 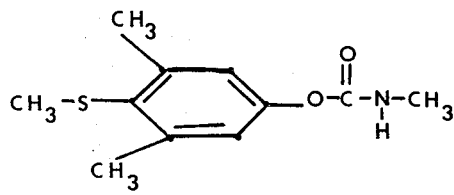<br>4-(Methylthio)-3,5-Xylylmethylcarbamate | 3,313,684 | MESUROL |
| 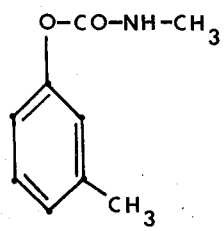<br>3-Methylphenyl-N-Methylcarbamate | | METACRATE |
| 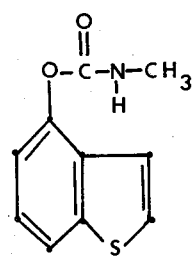<br>4-Benzothienyl-N-Methylcarbamate | 3,288,673<br>3,288,808 | MOBAM |

| Compound | U.S. Patent No. | Trademark |
|---|---|---|
| 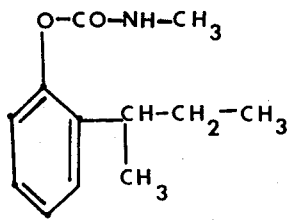<br>2-sec Butyl phenyl-N-Methylcarbamate | | OSBAC |
| 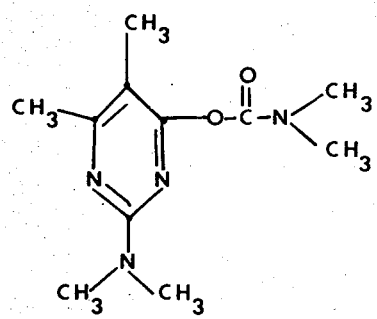<br>2-Dimethylamino 5,6-dimethyl-pyrimidin-4 yl Dimethylcarbamate | 3,493,574<br>3,577,543 | PIRIMOR |
| 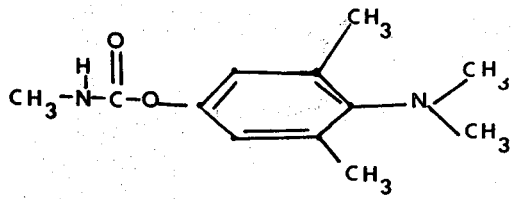<br>4-Dimethylamino 3,5-xylyl-Methylcarbamate | 3,084,098 | ZECTRAN |

In addition, there is also a limited number of oxime-carbamates in use, such as, for example:

| Compound | U.S. Patent No. | Trademark |
|---|---|---|
| CH₃S<br>    ＞C=NOCONHCH₃<br>CH₃ | | METHOMYL |
| CH₃<br>CH₃SĊC=NOCONHCH₃<br>   H<br>CH₃ | 3,217,037 | TEMIK |

However, the present oxime-carbamates, which may also be described as dihydropyrazinone oxime carbamates are novel compounds which display exceptional insectidical activity.

SUMMARY OF THE INVENTION

The present invention relates to novel oxime-carbamates and to the use of these compounds in the control of insects and acarids. The compounds of particular interest are those represented by the formula

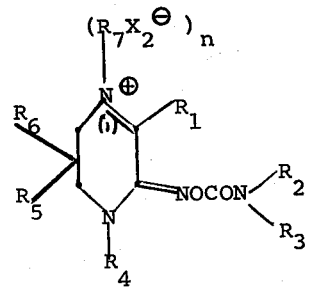

where
R₁ is —CH₃, —CH(CH₃)₂,

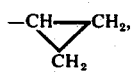

—C(CH₃)₃, or —C₆H₅;
R₂ is —H or —CH₃;
R₃ is —CH₃, —CH₂CH₃, —(CH₂)₂CH₃, —(CH₂)₃CH₃, —CH₂CH₂Cl or —C₆H₅;
R₄ is —H, —CH₃, —CH₂CH₃, —(CH₂)₂CH₃, —CH(CH₃)₂, —(CH₂)₃CH₃, —CH₂CH=CH₂, —CH₂C≡CH, —C₆H₅,

—CH₂CH—CH₂Cl,  —CH₂C=CHCl,
    |                    |
    Cl                   Cl

—CH(OH)CCl₃, —CH₂CH₂X₁, whereas X₁ is —Cl, —Br, —NH₂, —OH, —OCOCH₃, —OCOCH₂Cl, or —OCONHCH₃;

R₅ and R₆ are each —H or —CH₃, with the proviso that when R₅ and R₆ are both CH₃ then both CH₃ groups may be on either the same carbon atom or on different carbon atoms.

R₇ is —H, —CH₃ or —CH₂C₆H₅;
X₂ is —Cl, —Br or —I; and
n is 0 or 1, with the proviso that when n is 1 then N bears a ⊕ charge and X₂ bears a ⊖ charge.

The present invention also provides a method for the control of insect and acarid infestation which comprises applying either to the locus of said infestation, or systematically, a pesticidally effective amount of an oxime-carbamate having the formula

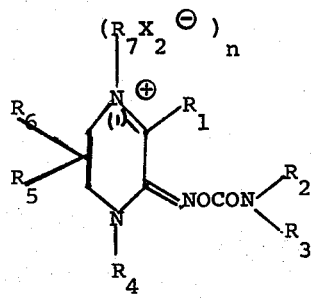

wherein R₁, R₂, R₃, R₄, R₅, R₆, R₇, X₂ and n have the meanings hereinbefore disclosed.

Illustrative examples of the oxime-carbamates encompassed within the above described general formula are the following compounds: (Note — the

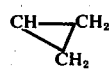

group is indicated as —△)

| Compound No. | Structure |
|---|---|
| 1 | [pyridine ring with CH₃ and NOCONHCH₃] |
| 2 | [pyridine ring with CH₃ and NOCON(CH₃)₂] |
| 3 | [pyridine ring with CH₃ and NOCONH(CH₂)₂CH₃] |
| 4 | [pyridine ring with CH₃ and NOCONHC₆H₅] |
| 5 | [pyridine ring with CH(CH₃)₂ and NOCONHCH₃] |
| 6 | [pyridine ring with cyclopropyl and NOCONHCH₃] |
| 7 | [pyridine ring with C₆H₅ and NOCONHCH₃] |
| 8 | [pyridine ring with CH₃, CH₃ and NOCONHCH₃] |

| Compound No. | Structure |
|---|---|
| 9 | 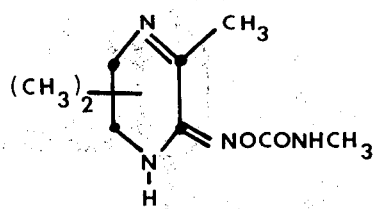 |
| 10 | 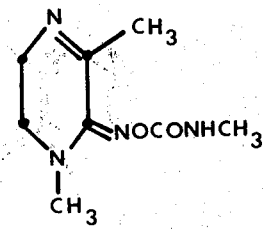 |
| 11 | 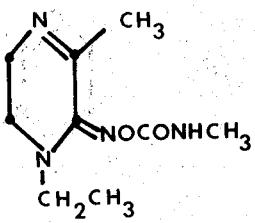 |
| 12 | 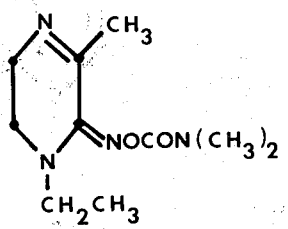 |
| 13 | 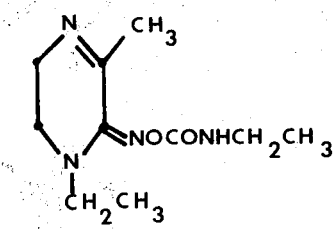 |
| 14 | 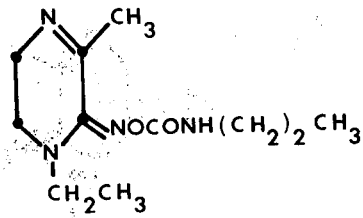 |
| Compound No. | Structure |
|---|---|
| 15 | 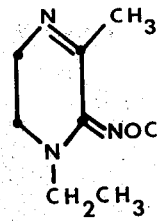 |
| 16 | 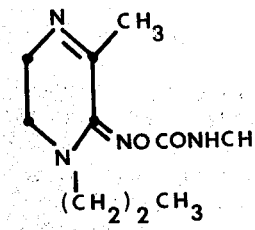 |
| 17 | 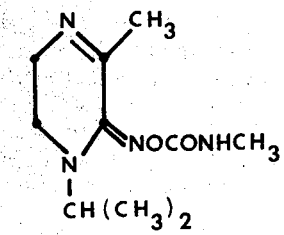 |
| 18 | 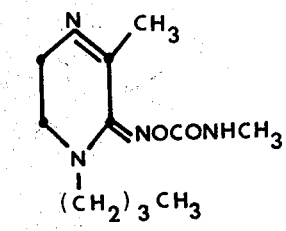 |
| 19 | 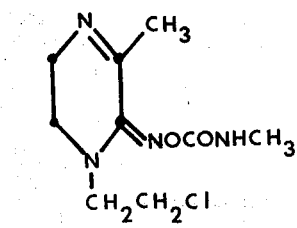 |
| 20 | 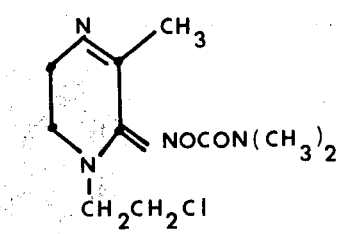 |

| Compound No. | Structure | Compound No. | Structure |
|---|---|---|---|
| 21 | 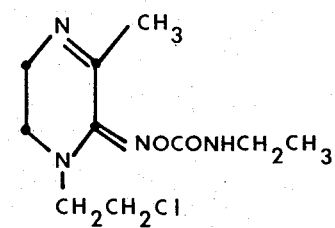 | 27 | 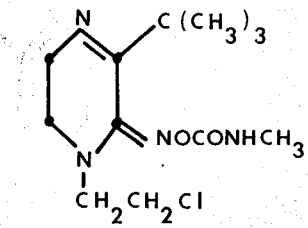 |
| 22 | 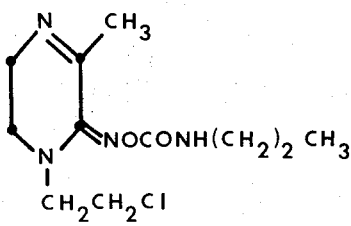 | 28 | 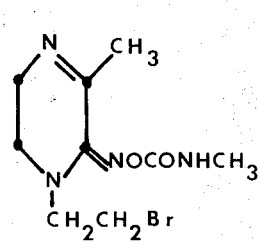 |
| 23 | 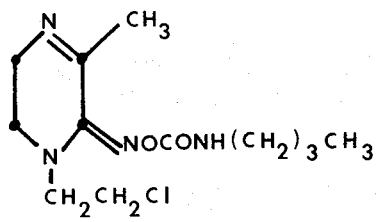 | 29 | 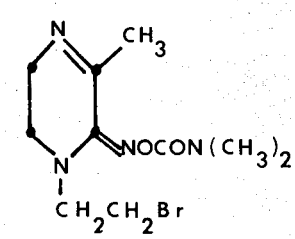 |
| 24 | 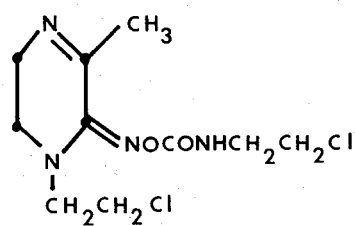 | 30 | 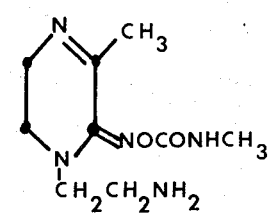 |
| 25 | 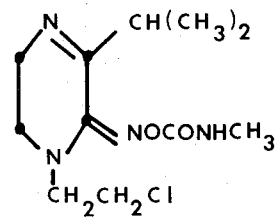 | 31 | 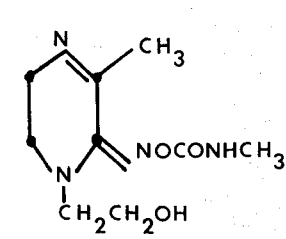 |
| 26 | 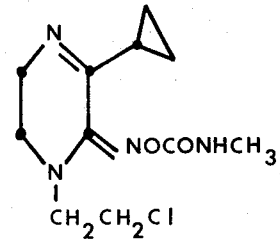 | 32 | 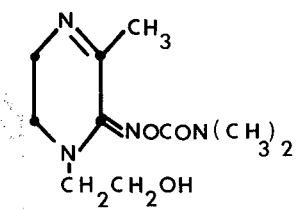 |

| Compound No. | Structure | Compound No. | Structure |
|---|---|---|---|
| 33 | 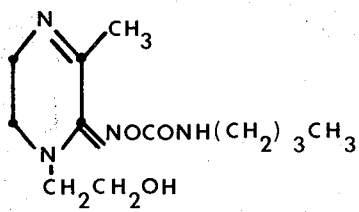 | 40 | 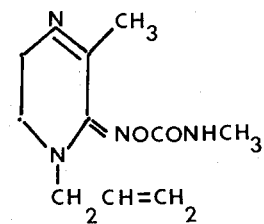 |
| 34 | 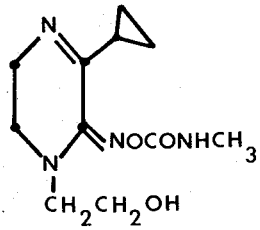 | 41 | 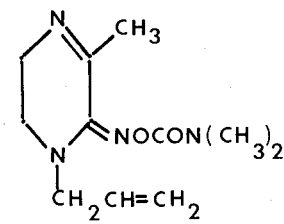 |
| 35 | 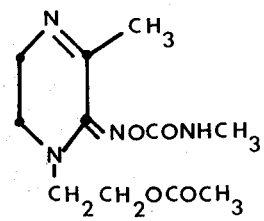 | 42 | 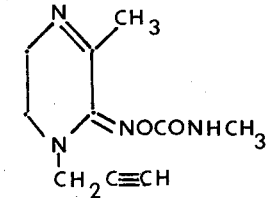 |
| 36 | 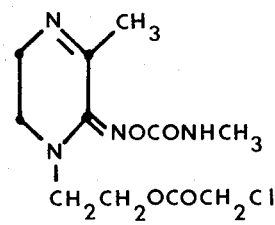 | 43 | 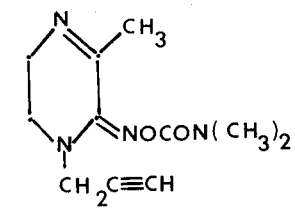 |
| 37 | 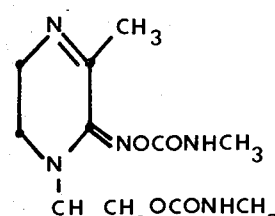 | 44 | 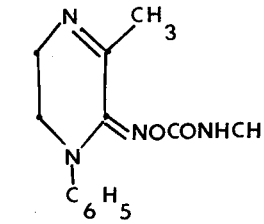 |
| 38 | 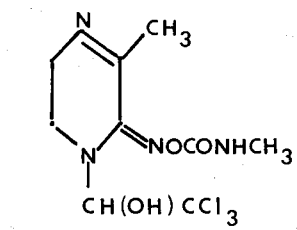 | 45 | 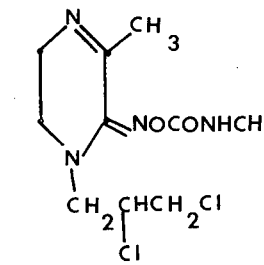 |
| 39 | 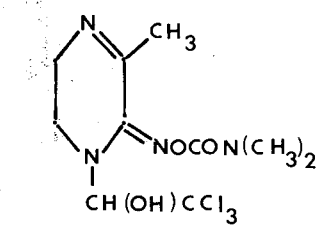 | 46 | 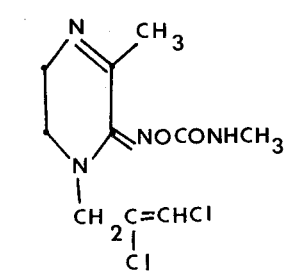 |

| Compound No. | Structure |
|---|---|
| 47 | 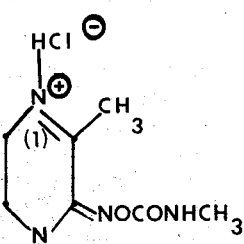 |
| 48 | 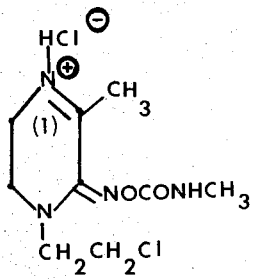 |
| 49 | 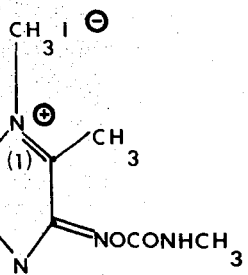 |
| 50 | 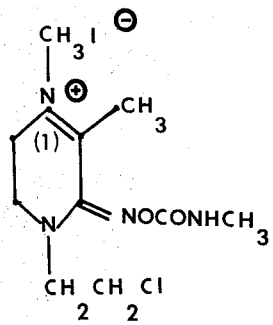 |
| 51 | 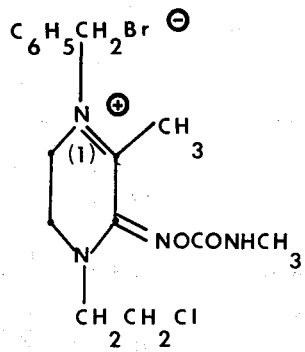 |
| 52 | 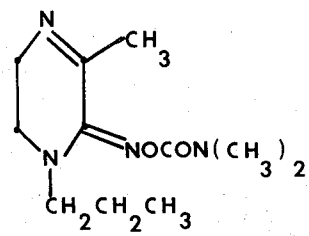 |

As hereinbefore stated, the compounds of the present invention are useful as insecticides and acaricides. They are conveniently applied to the locus of infestation in a variety of ways, for example, as a solution in an organic solvent, as an emulsion, as a spray, on an inert carrier such as clay, kaolin, talc, bentonite, attapulgite, or diatomaceous earth and the like, or as a formulated product in liquid or solid form. The present compounds may also be applied systemically in the same variety of ways. Useful organic solvents are the aromatics such as toluene, xylene, benzene, cyclohexane, and alkylated coal tar distillates, aliphatics such as naphthas and petroleum distillates, and various combinations of alcohols, esters, ketones and chlorinated compounds. The present insecticides may be provided as concentrated wettable powders containing as much as 80–90% active ingredient, or as concentrates in solid, liquid, or paste form containing 25–75% by weight of toxicant which may be diluted for application as desired, or as formulated products containing as little as about 5–10% active ingredient.

PREPARATION

The oxime-carbamates of this invention are prepared by utilizing the following general reaction employing the indicated reactants:

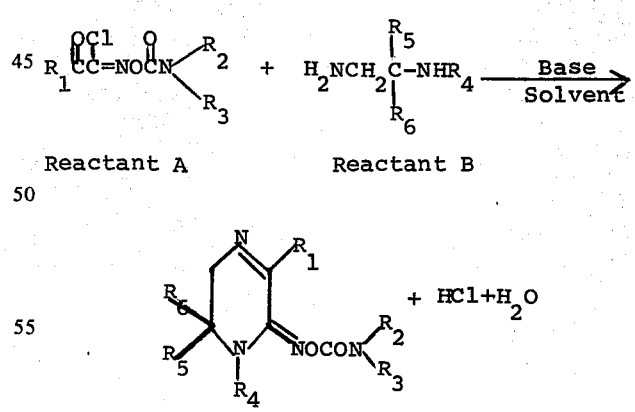

where $R_1$, $R_2$, $R_3$, $R_4$, $R_5$ and $R_6$ have the meanings hereinbefore described.

By varying Reactant B so that $R_5$ and $R_6$ are on the same or adjacent carbon atoms, it is possible to prepare compounds in which $R_5$ and $R_6$ are on the same or adjacent carbon atoms.

Reactants A (Chloro-oxime carbamates) are conveniently prepared by known methods. Reactants B (ethylenediamines), may be utilized as either the dihydrochloride salts or as the free bases. They too are prepared by known methods or purchased commercially.

The foregoing General Reaction is illustrated by Example 1 which describes the preparation of Compound No. 1.

EXAMPLE 1

A solution of 20 g. (0.112 mole) of 1-acetyl-1-chloroformaldoxime-N-methylcarbamate (Reactant A) in 200 ml. methanol was stirred in an ice bath while 13.4 g. (0.224 mole) of ethylenediamine (Reactant B) was added. After stirring for 30 minutes at ambient temperature, the reaction mixture was evaporated to dryness under reduced pressure. Chloroform (200 ml.) was added and the precipitated ethylenediamine hydrochloride removed by filtration. The filtrate was evaporated to dryness and the residue extracted with boiling ethyl acetate. The extract was evaporated and the extraction process repeated with benzene. Cooling of the hot benzene extract and filtration provided 13.1 g. (63%) of Compound No. 1 as a light yellow solid, m.p. 129°–130°C.

EXAMPLES 2–7

The following table, Table 1, summarizes the preparation of Compound Nos. 2–7 by the same procedure as set forth in Example 1, with the exception that the reactants A and B were varied as indicated.

In those instances where the product does not solidify, it is purified by silica gel chromatography.

EXAMPLE 8

Compound No. 11 was prepared in the following manner: A solution of 5.0 g. (0.028 mole) of 1-acetyl-1-chloroformaldoxime-N-methylcarbamate (Reactant A) in 20 ml. of chloroform (or methanol) was added to a stirred mixture of 2.47 g. (0.028 mole) of N-ethylethylenediamine (Reactant B) and 10 g. of anhydrous potassium carbonate in 30 ml. of chloroform at 5°–10°C. The reaction was stirred 4 hours at room temperature, 2 g. of magnesium sulfate was added and the mixture filtered. The filtrate was evaporated to dryness giving 7.4 g. of an oil which was redissolved in chloroform, washed with water, and dried over magnesium sulfate. After removal of the solvent, the solid was slurried in petroleum ether to give 4.75 grams (80%) of Compound No. 11 as a cream-colored solid, mp 68°–72°C. In those instances where the product does not solidify, it is purified by column chromatography.

EXAMPLES 9–28

The following table, Table 2, summarizes the preparation of Compound Nos. 8–10, 12–18, 30–34, 40–44, and 52 by the procedure set forth in Example 8, except that the Reactants A and B were varied as indicated.

Table 1

| Example | Reactants A | B | Product (Compound No.) |
|---|---|---|---|
| 2 | $CH_3\overset{O}{\overset{\|}{C}}-\overset{Cl}{\overset{\|}{C}}=NOCON(CH_3)_2$ | $H_2NCH_2CH_2NH_2$ | 2 |
| 3 | $CH_3\overset{O}{\overset{\|}{C}}-\overset{Cl}{\overset{\|}{C}}=NOCONH(CH_2)_2CH_3$ | " | 3 |
| 4 | $CH_3\overset{O}{\overset{\|}{C}}-\overset{Cl}{\overset{\|}{C}}=NOCONHC_6H_5$ | " | 4 |
| 5 | $(CH_3)_2CH\overset{O}{\overset{\|}{C}}-\overset{Cl}{\overset{\|}{C}}=NOCONHCH_3$ | " | 5 |
| 6 | $\triangleright\!-\overset{O}{\overset{\|}{C}}-\overset{Cl}{\overset{\|}{C}}-NOCONHCH_3$ | " | 6 |
| 7 | $C_6H_5\overset{O}{\overset{\|}{C}}-\overset{Cl}{\overset{\|}{C}}=NOCONHCH_3$ | " | 7 |

Table 2

| Example | Reactants A | B | Product (Compound No.) |
|---|---|---|---|
| 9 | $CH_3\overset{O}{\overset{\|}{C}}-\overset{Cl}{\overset{\|}{C}}=NOCONHCH_3$ | $CH_3\overset{NH_2}{\overset{\|}{C}}HCH_2NH_2$ | 8 |
| 10 | " | $(CH_3)_2\overset{NH_2}{\overset{\|}{C}}-CH_2NH_2$ | 9 |
| 11 | $CH_3\overset{O}{\overset{\|}{C}}-\overset{Cl}{\overset{\|}{C}}=NOCONHCH_3$ | $CH_3NHCH_2CH_2NH_2$ | 10 |
| 12 | $CH_3\overset{O}{\overset{\|}{C}}-\overset{Cl}{\overset{\|}{C}}=NOCON(CH_3)_2$ | $CH_3CH_2NHCH_2CH_2NH_2$ | 12 |

Table 2-continued

| Example | Reactants A | Reactants B | Product (Compound No.) |
|---|---|---|---|
| 13 | CH₃C(O)-C(Cl)=NOCONHCH₂CH₃ | " | 13 |
| 14 | CH₃C(O)-C(Cl)=NOCONH(CH₂)₂CH₃ | " | 14 |
| 15 | CH₃C(O)-C(Cl)=NOCONHCH₂CH₂Cl | " | 15 |
| 16 | CH₃C(O)-C(Cl)=NOCONHCH₃ | CH₃(CH₂)₂NHCH₂CH₂NH₂ | 16 |
| 17 | " | (CH₃)₂CHNHCH₂CH₂NH₂ | 17 |
| 18 | CH₃C(O)-C(Cl)=NOCONHCH₃ | CH₃(CH₂)₃NHCH₂CH₂NH₂ | 18 |
| 19 | CH₃C(O)-C(Cl)=NOCONHCH₃ | H₂NCH₂CH₂NHCH₂CH₂NH₂ | 30 |
| 20 | CH₃C(O)-C(Cl)=NOCONHCH₃ | HOCH₂CH₂NHCH₂CH₂NH₂ | 31 |
| 21 | CH₃C(O)-C(Cl)=NOCON(CH₃)₂ | " | 32 |
| 22 | CH₃C(O)-C(Cl)=NOCONH(CH₂)₃CH₃ | " | 33 |
| 23 | (cyclopropyl)-C(O)-C(Cl)=NOCONHCH₃ | " | 34 |
| 24 | CH₃C(O)-C(Cl)=NOCONHCH₃ | CH₂=CHCH₂NHCH₂CH₂NH₂ | 40 |
| 25 | CH₃C(O)-C(Cl)=NOCON(CH₃)₂ | CH₂=CHCH₂NHCH₂CH₂NH₂ | 41 |
| 26 | CH₃C(O)-C(Cl)=NOCONHCH₃ | CH≡CCH₂NHCH₂CH₂NH₂ | 42 |
| 27 | CH₃C(O)-C(Cl)=NOCON(CH₃)₂ | " | 43 |
| 28 | CH₃C(O)-C(Cl)=NOCONHCH₃ | C₆H₅NHCH₂CH₂NH₂ | 44 |
| 28A | CH₃C(O)-C(Cl)=NOCON(CH₃)₂ | CH₃CH₂CH₂NHCH₂CH₂NH₂ | 52 |

EXAMPLE 29

Compound No. 19 was prepared in the following manner: A suspension of 5.0 g. (0.028 mole) of 1-acetyl-1-chloroformaldoxime-N-methylcarbamate (Reactant A), 5.75 g. (0.029 mole) of N-(2-chloroethyl)-ethylenediamine dihydrochloride (Reactant B) and 2.5 g of magnesium sulfate in 30 ml. of tetrahydrofuran was stirred at 5°–10°C. and treated slowly with a solution of 12.5 ml. of triethylamine in 20 ml. of tetrahydrofuran. After the addition was completed, the reaction mixture was stirred 4 hours at room temperature, filtered and the filtrate evaporated to dryness giving 6.8 g. (98.5%) of oil which solidified on standing. The crude product was purified by redissolving in chloroform, washing with water, drying over magnesium sulfate, concentrating and slurrying the resulting solid with diethyl ether to give 3.9 g. (57%) of Compound No. 19 as a light yellow solid, m.p. 98°–100°C.

EXAMPLES 30–39

Compounds 20–29 were prepared according to the procedure set forth in Example 29, except that the Reactants A and B were varied as indicated in Table 3.

Table 3

| Example | Reactants A | B | Product (Compound No.) |
|---|---|---|---|
| 30 | CH$_3$—C(=O)—C(Cl)=NOCONHCH$_3$ | ClCH$_2$CH$_2$NHCH$_2$CH$_2$NH$_2$·2HCl | 20 |
| 31 | CH$_3$—C(=O)—C(Cl)=NOCONHCH$_2$CH$_3$ | " | 21 |
| 32 | CH$_3$—C(=O)—C(Cl)=NOCONH(CH$_2$)$_2$CH$_3$ | " | 22 |
| 33 | CH$_3$—C(=O)—C(Cl)=NOCONH(CH$_2$)$_3$CH$_3$ | " | 23 |
| 34 | CH$_3$—C(=O)—C(Cl)=NOCONHCH$_2$CH$_2$Cl | " | 24 |
| 35 | (CH$_3$)$_2$CH—C(=O)—C(Cl)=NOCONHCH$_3$ | " | 25 |
| 36 | ▷—C(=O)—C(Cl)=NOCONHCH$_3$ | " | 26 |
| 37 | (CH$_3$)$_3$—C(=O)—C(Cl)=NOCONHCH$_3$ | " | 27 |
| 38 | CH$_3$—C(=O)—C(Cl)=NOCONHCH$_3$ | BrCH$_2$CH$_2$NHCH$_2$CH$_2$NH$_2$·2HBr | 28 |
| 39 | CH$_3$C(=O)—C(Cl)=NOCON(CH$_3$)$_2$ | " | 29 |

EXAMPLE 40

Compound No. 36 was prepared in the following manner: A suspension of 2.28 g. (0.01 mole) of Compound No. 31 in 40 ml. of dichloromethane was cooled to 0°C. and treated with 1.39 ml. (1.01 g., 0.01 mole) of triethylamine. A solution of 0.79 ml. (1.13 g., 0.01 mole) of chloroacetyl chloride in 5 ml. of dichloromethane was then added dropwise, the reaction temperature being maintained at 0°C. After the mixture was allowed to warm to room temperature the solvent was evaporated. The residue was taken up in tetrahydrofuran and the amine salt removed by filtration. Evaporation of the solvent from the filtrate produced 3.8 g. of oil which was purified by chromatography over Florisil (20 g. packed in benzene) using chloroform as the eluting solvent. The product fractions were evaporated to dryness giving 0.94 g. of Compound No. 36 as a colorless oil. Alternatively the product could be purified by extraction of a benzene-dichloromethane (2:1) solution thereof with water followed by drying and concentrating the organic phase.

EXAMPLE 41

Compound No. 35 was prepared according to the procedure of Example 40, except that CH$_3$COCl was used instead of chloroacetyl chloride.

EXAMPLE 42

Compound No. 37 was prepared according to the procedure of Example 40 except that CH$_3$NCO was used instead of chloroacetyl chloride.

EXAMPLE 43

Compound No. 38 was prepared in the following manner: A mixture of 5.0 g. (0.027 mole) of Compound No. 1 and 4.0 g. (0.027 mole) of chloral in 30 ml. of benzene was stirred 12 hours at room temperature and filtered providing 8.7 g. (97%) of Compound No. 38 as a white solid, m.p. 155°–156°C.

EXAMPLE 44

Compound No. 39 was prepared according to the procedure of Example 43, except that Compound No. 2 (instead of Compound No. 1) was treated with chloral as set forth therein.

EXAMPLE 45

Compound No. 45 was prepared as follows: A solution of 3.0 g. (0.0134 mole) of Compound No. 40 in 30 ml. of chloroform was cooled to 0°C. and treated cautiously with a solution of 1.4 g. of chlorine in 20 ml. of chloroform at 0°C. After the excess chlorine as removed, the reaction mixture was cooled to 5°C. and 20 g. of potassium carbonate was added followed by 5 ml. of water. The mixture was then filtered and evaporated to dryness leaving 3.8 g. of syrup which was purified by dissolving in 8 ml. of ethyl acetate and passing through a chromatographic column containing 40 g. of silica gel. The product was eluted with ethyl acetate-methanol (20:1). Evaporation of the solvent gave 1.4 g. of Compound No. 45 as a waxy semi-solid.

EXAMPLE 46

Compound No. 46 was prepared according to the procedure of Example 45, except that Compound 42 (instead of Compound No. 40) was treated with chlorine as set forth therein.

EXAMPLE 47

Compound No. 47 was prepared as follows: A solution of 5.0 g. (0.027 mole) of Compound No. 1 in 100 ml. of ethyl acetate was saturated with anhydrous hydrogen chloride. The resulting suspension was filtered and the hygroscopic solid dried in a vacuum desiccator affording 5.9 g. (99%) of Compound No. 47 as a cream-colored solid, m.p. 150°–155°C.

EXAMPLE 48

Compound No. 48 was prepared according to the procedure of Example 47 except that Compound No. 19 (instead of Compound No. 1) was treated with anhydrous hydrogen chloride.

EXAMPLE 49

Compound No. 49 was prepared as follows: A solution of 1.0 g. of Compound No. 1 in 5 ml. of ethyl acetate (or acetonitrile) and 2 ml. of methyl iodide was stirred overnight at room temperature, diluted with ethyl ether and the precipitated solid collected by filtration yielding 1.5 g. of Compound No. 49 as a light yellow solid, m.p. 185°–190°C.

EXAMPLE 50

Compound No. 50 was prepared according to the procedure of Example 49, except that Compound No. 19 (instead of Compound No. 1) was treated with methyl iodide as set forth therein.

EXAMPLE 51

Compound No. 51 was prepared by the procedure of Example 49, except that Compound 19 (instead of Compound No. 1) was treated with $C_6H_5CH_2Br$.

EFFICACY

The insecticidal and acaricidal activities of representative and typical oxime carbamates of this invention were determined according to the following described methods.

Test formulations of candidate samples were prepared by dissolving each candidate compound in acetone containing small amounts of emulsifier. The test formulations (solutions) were then diluted with water to obtain the desired active ingredient concentration. Where solubility was a problem, the diluted test formulation was wet ball-milled.

EXAMPLES 52–153A

TEST ORGANISMS

Southern Armyworm — (*Prodenia eridania*), and Mexican Bean Beetle — (*Epilachna varivestis*)

Lima bean leaves dipped into test solutions of the respective compounds were offered to ten larvae of the Southern Armyworm (late third instar) and the Mexican Bean Bettle (late second instar) for a 48-hour feeding period. Mortality data were recorded. In these tests, as in tests against all other organisms, untreated controls were included for comparative purposes.

Tables 4 and 5 summarize the activity of the indicated oxime carbamates against Southern Armyworms and Mexican Bean Beetles respectively. Blank spaces in these subsequent Tables mean that no tests were conducted at the corresponding particular concentrations.

TABLE 4

Test Organism: Southern Armyworm (Prodenia eridania)

| Example No. | Compound No. | Percent Mortality Application Concentration | | | |
|---|---|---|---|---|---|
| | | 0.1 | 0.05 | 0.01 | 0.005 |
| 52 | 1 | 100 | 100 | 0 | |
| 53 | 2 | 0 | | | |
| 54 | 3 | 0 | | | |
| 55 | 4 | 0 | | | |
| 56 | 5 | 0 | | | |
| 57 | 6 | 40 | | | |
| 58 | 7 | 0 | | | |
| 59 | 8 | 100 | 100 | 90 | 40 |
| 60 | 9 | 100 | 100 | 20 | |
| 61 | 10 | 100 | 100 | 0 | |
| 62 | 11 | 100 | 90 | 0 | |
| 63 | 12 | 80 | | | |
| 64 | 13 | 90 | 90 | 10 | |
| 65 | 14 | 0 | | | |
| 66 | 15 | 0 | | | |
| 67 | 16 | 100 | 100 | 80 | 50 |
| 68 | 17 | 60 | | | |
| 69 | 18 | 70 | | | |
| 70 | 19 | 100 | 100 | 70 | 40 |
| 71 | 20 | 40 | | | |
| 72 | 21 | 30 | | | |
| 73 | 22 | 0 | | | |
| 74 | 23 | 0 | | | |
| 75 | 24 | 0 | | | |
| 76 | 25 | 0 | | | |
| 77 | 26 | 0 | | | |
| 78 | 27 | 0 | | | |
| 79 | 28 | 100 | 80 | 60 | 0 |
| 80 | 29 | 0 | | | |
| 81 | 30 | 0 | | | |
| 82 | 31 | 50 | | | |
| 83 | 32 | 0 | | | |
| 84 | 33 | 0 | | | |
| 85 | 34 | 0 | | | |
| 86 | 35 | 0 | | | |
| 87 | 36 | 0 | | | |
| 88 | 37 | 0 | | | |
| 89 | 38 | 0 | | | |
| 90 | 39 | 0 | | | |
| 91 | 40 | 100 | 90 | 0 | |
| 92 | 41 | 0 | | | |
| 93 | 42 | 100 | 100 | 60 | 20 |
| 94 | 43 | 0 | | | |
| 95 | 44 | 0 | | | |
| 96 | 45 | 0 | | | |
| 97 | 46 | 10 | | | |
| 98 | 47 | 50 | | | |
| 99 | 48 | | | | |
| 100 | 49 | 100 | 80 | 0 | |
| 101 | 50 | 100 | 60 | 0 | |
| 102 | 51 | 0 | | | |
| 102A | 52 | 60 | | | |
| Untreated | — | 0 | 0 | 0 | 0 |

TABLE 5

Test Organism: Mexican Bean Beetle (Epilachna varivestis)

| Example No. | Compound No. | Percent Mortality Application Concentration | | | | | |
|---|---|---|---|---|---|---|---|
| | | 0.1 | 0.05 | 0.01 | 0.005 | 0.001 | 0.0005 |
| 103 | 1 | 100 | 90 | 0 | | | |
| 104 | 2 | 0 | | | | | |
| 105 | 3 | 0 | | | | | |
| 106 | 4 | 0 | | | | | |
| 107 | 5 | 70 | | | | | |
| 108 | 6 | 60 | | | | | |
| 109 | 7 | 0 | | | | | |
| 110 | 8 | 100 | 100 | 100 | 100 | 10 | |
| 111 | 9 | 100 | 100 | 50 | | | |
| 112 | 10 | 100 | 100 | 100 | 100 | 0 | |
| 113 | 11 | 100 | 100 | 50 | | | |
| 114 | 12 | 100 | 90 | 10 | | | |
| 115 | 13 | 100 | 90 | 70 | 50 | | |
| 116 | 14 | 100 | 100 | 50 | 50 | | |

TABLE 5-continued

Test Organism: Mexican Bean Beetle (Epilachna varivestis)
Percent Mortality
Application Concentration

| Example No. | Compound No. | 0.1 | 0.05 | 0.01 | 0.005 | 0.001 | 0.0005 |
|---|---|---|---|---|---|---|---|
| 117 | 15 | 0 | | | | | |
| 118 | 16 | 100 | 100 | 100 | 90 | 50 | |
| 119 | 17 | 20 | | | | | |
| 120 | 18 | 80 | | | | | |
| 121 | 19 | 100 | 100 | 100 | 100 | 80 | 40 |
| 122 | 20 | 80 | | | | | |
| 123 | 21 | 70 | | | | | |
| 124 | 22 | 100 | 40 | | | | |
| 125 | 23 | 0 | | | | | |
| 126 | 24 | 40 | | | | | |
| 127 | 25 | 100 | 20 | | | | |
| 128 | 26 | 0 | | | | | |
| 129 | 27 | 0 | | | | | |
| 130 | 28 | 100 | 100 | 60 | 50 | | |
| 131 | 29 | 60 | | | | | |
| 132 | 30 | 0 | | | | | |
| 133 | 31 | 0 | | | | | |
| 134 | 32 | 0 | | | | | |
| 135 | 33 | 0 | | | | | |
| 136 | 34 | 0 | | | | | |
| 137 | 35 | 0 | | | | | |
| 138 | 36 | 0 | | | | | |
| 139 | 37 | 0 | | | | | |
| 140 | 38 | 0 | | | | | |
| 141 | 39 | 0 | | | | | |
| 142 | 40 | 100 | 100 | 40 | 20 | | |
| 143 | 41 | 70 | | | | | |
| 144 | 42 | 100 | 100 | 100 | 100 | 40 | |
| 145 | 43 | 80 | | | | | |
| 146 | 44 | 0 | | | | | |
| 147 | 45 | 0 | | | | | |
| 148 | 46 | 80 | | | | | |
| 149 | 47 | 80 | | | | | |
| 150 | 48 | | | | | | |
| 151 | 49 | 70 | | | | | |
| 152 | 50 | 0 | | | | | |
| 153 | 51 | 0 | | | | | |
| 153A | 52 | 100 | 20 | | | | |
| Untreated | — | 0 | 0 | 0 | 0 | 0 | 0 |

EXAMPLES 154–255A

Test Organism — Pea Aphid — (*Macrosiphum pisi*)
Contact Test

Ten adult pea aphids were sprayed with representative compounds of this invention diluted to the desired concentration and transferred to similarly sprayed pea plants. After a culture period of 48 hours, mortality determinations were made. The results are set forth in Table 6.

Systemic Test

To the vermiculite substratum of potted pea seedlings there is applied 25 ml. of the candidate chemical which has been diluted in a suitable non-phytotoxic solvent. Three days after treatment the pea plants are infested with ten adult pea aphids (Macrosiphum pisi). Mortality determinations are made after five days. The results are set forth in Table 7.

TABLE 6

Test Organism: Pea Aphid (contact) (Macrosiphum pisi)

Percent Mortality

| No. | No. | 0.1 | 0.05 | 0.01 | 0.005 | 0.001 | 0.0005 | 0.0001 | 0.00005 | 0.00001 |
|---|---|---|---|---|---|---|---|---|---|---|
| 154 | 1 | 100 | 100 | 100 | 20 | | | | | |
| 155 | 2 | 100 | 100 | 50 | | | | | | |
| 156 | 3 | 60 | | | | | | | | |
| 157 | 4 | 0 | | | | | | | | |
| 158 | 5 | 90 | 20 | | | | | | | |
| 159 | 6 | 100 | 100 | 20 | | | | | | |
| 160 | 7 | 40 | | | | | | | | |
| 161 | 8 | 100 | 100 | 50 | | | | | | |
| 162 | 9 | 100 | 100 | 100 | 100 | 50 | | | | |
| 163 | 10 | 100 | 100 | 100 | 100 | 30 | | | | |
| 164 | 11 | 100 | 100 | 100 | 100 | 100 | 100 | 100 | 40 | |
| 165 | 12 | 100 | 100 | 100 | 100 | 100 | 90 | 30 | 30 | |
| 166 | 13 | 100 | 100 | 100 | 100 | 100 | 70 | 50 | | |
| 167 | 14 | 100 | 100 | 100 | 50 | | | | | |
| 168 | 15 | 100 | 100 | 80 | 40 | | | | | |
| 169 | 16 | 100 | 100 | 100 | 100 | 100 | 100 | 50 | | |
| 170 | 17 | 100 | 100 | 100 | 100 | 100 | 90 | 20 | | |
| 171 | 18 | 100 | 100 | 100 | 40 | | | | | |
| 172 | 19 | 100 | 100 | 100 | 100 | 100 | 100 | 80 | 15 | |
| 173 | 20 | 100 | 100 | 100 | 100 | 100 | 100 | 100 | 40 | |
| 174 | 21 | 100 | 100 | 100 | 100 | 70 | 50 | 20 | | |
| 175 | 22 | 100 | 100 | 100 | 30 | | | | | |
| 176 | 23 | 100 | 80 | 60 | 10 | | | | | |
| 177 | 24 | 100 | 100 | 100 | 100 | 0 | | | | |
| 178 | 25 | 100 | 100 | 60 | | | | | | |
| 179 | 26 | 20 | | | | | | | | |
| 180 | 27 | 100 | 80 | 0 | | | | | | |
| 181 | 28 | 100 | 100 | 100 | 100 | 100 | 100 | 50 | | |
| 182 | 29 | 100 | 100 | 100 | 100 | 100 | 40 | | | |

TABLE 6-continued

Test Organism: Pea Aphid (contact) (Macrosiphum pisi)

Percent Mortality

| No. | No. | 0.1 | 0.05 | 0.01 | 0.005 | 0.001 | 0.0005 | 0.0001 | 0.00005 | 0.00001 |
|---|---|---|---|---|---|---|---|---|---|---|
| 183 | 30 | 30 | | | | | | | | |
| 184 | 31 | 100 | 100 | 60 | | | | | | |
| 185 | 32 | 100 | 100 | 30 | | | | | | |
| 186 | 33 | 100 | 40 | 0 | | | | | | |
| 187 | 34 | 100 | 100 | 50 | | | | | | |
| 188 | 35 | 100 | 100 | 100 | 10 | | | | | |
| 189 | 36 | 100 | 100 | 60 | | | | | | |
| 190 | 37 | 100 | 50 | 0 | | | | | | |
| 191 | 38 | 10 | | | | | | | | |
| 192 | 39 | 0 | | | | | | | | |
| 193 | 40 | 100 | 100 | 100 | 100 | 100 | 100 | 50 | | |
| 194 | 41 | 100 | 80 | 50 | | | | | | |
| 195 | 42 | 100 | 100 | 100 | 100 | 30 | | | | |
| 196 | 43 | 100 | 100 | 100 | 100 | 100 | 30 | | | |
| 197 | 44 | 80 | | | | | | | | |
| 198 | 45 | 100 | 100 | 100 | 60 | | | | | |
| 199 | 46 | 100 | 100 | 100 | 40 | | | | | |
| 200 | 47 | 100 | 100 | 60 | | | | | | |
| 201 | 48 | | | | | 100 | 100 | 50 | | |
| 202 | 49 | 10 | | | | | | | | |
| 203 | 50 | 90 | 60 | 0 | | | | | | |
| 204 | 51 | 100 | 100 | 90 | 50 | | | | | |
| 204A | 52 | 100 | 100 | 100 | 100 | 100 | 100 | 100 | 100 | |
| Untreated | — | 0 | 0 | 0 | 0 | 0 | 0 | 0 | 0 | |

TABLE 7

Test Organism: Pea Aphid (Systemic) (Macrosiphum pisi)

Percent Mortality Application Concentration

| Example No. | Compound No. | 0.1 | 0.05 | 0.01 | 0.005 | 0.001 | 0.0005 | 0.0001 |
|---|---|---|---|---|---|---|---|---|
| 205 | 1 | 100 | 100 | 40 | | | | |
| 206 | 2 | 0 | | | | | | |
| 207 | 3 | 0 | | | | | | |
| 208 | 4 | 0 | | | | | | |
| 209 | 5 | 0 | | | | | | |
| 210 | 6 | 0 | | | | | | |
| 211 | 7 | 0 | | | | | | |
| 212 | 8 | 0 | | | | | | |
| 213 | 9 | 100 | | 0 | | | | |
| 214 | 10 | 0 | | | | | | |
| 215 | 11 | 100 | 100 | 100 | 20 | | | |
| 216 | 12 | 100 | | | 100 | 50 | | |
| 217 | 13 | 100 | | | 100 | 0 | | |
| 218 | 14 | 100 | | | 40 | 10 | | |
| 219 | 15 | 0 | | | | | | |
| 220 | 16 | 100 | | | 60 | 0 | | |
| 221 | 17 | 100 | | | 100 | 0 | 0 | |
| 222 | 18 | 80 | | | | | | |
| 223 | 19 | 100 | 100 | 100 | 0 | | | |
| 224 | 20 | 100 | 100 | 100 | 100 | 100 | 40 | |
| 225 | 21 | 100 | | 0 | | | | |
| 226 | 22 | 0 | | | | | | |
| 227 | 23 | 0 | | | | | | |
| 228 | 24 | 0 | | | | | | |
| 229 | 25 | 0 | | | | | | |
| 230 | 26 | 0 | | | | | | |
| 231 | 27 | 0 | | | | | | |
| 232 | 28 | 100 | 100 | 40 | 0 | | | |
| 233 | 29 | 100 | | 100 | 10 | 0 | | |
| 234 | 30 | 0 | | | | | | |
| 235 | 31 | 0 | | | | | | |
| 236 | 32 | 0 | | | | | | |
| 237 | 33 | 0 | | | | | | |
| 238 | 34 | 0 | | | | | | |
| 239 | 35 | 0 | | | | | | |
| 240 | 36 | 0 | | | | | | |
| 241 | 37 | 0 | | | | | | |
| 242 | 38 | 0 | | | | | | |
| 243 | 39 | 0 | | | | | | |
| 244 | 40 | 100 | | 100 | 60 | 30 | | |
| 245 | 41 | 0 | | | | | | |
| 246 | 42 | 100 | | 100 | 100 | 0 | | |
| 247 | 43 | 100 | | 90 | 60 | 0 | | |
| 248 | 44 | 0 | | | | | | |
| 249 | 45 | 0 | | | | | | |
| 250 | 46 | 90 | | | 0 | | | |
| 251 | 47 | 60 | | | | | | |
| 252 | 48 | | | | | | | |
| 253 | 49 | 10 | | | | | | |
| 254 | 50 | 0 | | | | | | |
| 255 | 51 | 0 | | | | | | |
| 255A | 52 | 100 | | | 100 | 100 | 100 | 10 |
| Untreated | — | 0 | 0 | 0 | 0 | 0 | 0 | 0 |

EXAMPLES 256–306A

Strawberry Mite — (*Tetranychus atlanticus*)

Excised lima bean plants were infested with 50 to 100 adults of the strawberry spider mite prior to testing. The infested plants were dipped into water dilutions of each test chemical. Treated test plants were allowed to dry and then cultured at room temperature. After 5 days, mortality counts were made. The results are noted in Table 8.

EXAMPLES 307–357A

Housefly — (*Musca domestica*)

Diluted samples were applied to houseflies in a contact test by means of the Waters vertical spray tower. The spray tower is operated at 10 psi and discharges about 28 ml. of material per minute through a glass atomizer. The spray descends through an 8 inch stainless steel cylinder to the plant or test insects 44 inches below the atomizer.

Fifty adult houseflies were sprayed in a 2 inches high by 5 inches diameter stainless steel cage faced on top and bottom with 14 mesh screen. The insects were retained in the same cages for knockdown observations. The 24-hour mortality of houseflies may be from residual as well as from direct contact. The percentages of knockdown and kill are summarized in Table 9.

TABLE 8

Test Organism: Strawberry Mite (Tetranchus atlanticus)

| Example No. | Compound No. | Percent Mortality Application Concentration | | | |
|---|---|---|---|---|---|
| | | 0.1 | 0.05 | 0.01 | 0.005 |
| 256 | 1 | 68 | 17 | | |
| 257 | 2 | 0 | | | |
| 258 | 3 | 0 | | | |
| 259 | 4 | 0 | | | |
| 260 | 5 | 0 | | | |
| 261 | 6 | 0 | | | |
| 262 | 7 | 0 | | | |
| 263 | 8 | 34 | | | |

TABLE 8-continued

Test Organism: Strawberry Mite (Tetranchus atlanticus)

| Example No. | Compound No. | Percent Mortality Application Concentration | | | |
|---|---|---|---|---|---|
| | | 0.1 | 0.05 | 0.01 | 0.005 |
| 264 | 9 | 22 | | | |
| 265 | 10 | 21 | | | |
| 266 | 11 | 100 | 20 | 0 | |
| 267 | 12 | 86 | | | |
| 268 | 13 | 35 | | | |
| 269 | 14 | 15 | | | |
| 270 | 15 | 12 | | | |
| 271 | 16 | 76 | | | |
| 272 | 17 | 100 | 43 | | |
| 273 | 18 | 54 | | | |
| 274 | 19 | 100 | 40 | 33 | 30 |
| 275 | 20 | 73 | | | |
| 276 | 21 | 20 | | | |
| 277 | 22 | 0 | | | |
| 278 | 23 | 0 | | | |
| 279 | 24 | 21 | | | |
| 280 | 25 | 0 | | | |
| 281 | 26 | 0 | | | |
| 282 | 27 | 0 | | | |
| 283 | 28 | 90 | 95 | 77 | 30 |
| 284 | 29 | 33 | | | |
| 285 | 30 | 0 | | | |
| 286 | 31 | 0 | | | |
| 287 | 32 | 0 | | | |
| 288 | 33 | 0 | | | |
| 289 | 34 | 0 | | | |
| 290 | 35 | 0 | | | |
| 291 | 36 | 15 | | | |
| 292 | 37 | 0 | | | |
| 293 | 38 | 0 | | | |
| 294 | 39 | 0 | | | |
| 295 | 40 | 88 | 52 | 10 | |
| 296 | 41 | 13 | | | |
| 297 | 42 | 95 | 43 | 25 | 0 |
| 298 | 43 | 90 | 45 | 42 | 0 |
| 299 | 44 | 0 | | | |
| 300 | 45 | 10 | | | |
| 301 | 46 | 83 | 87 | 15 | |
| 302 | 47 | 64 | | | |
| 303 | 48 | | | | |
| 304 | 49 | 97 | 94 | 35 | |
| 305 | 50 | 0 | | | |
| 306 | 51 | 0 | | | |
| 306A | 52 | 86 | | | |
| Untreated | — | 0 | 0 | 0 | 0 |

TABLE 9

Test Organism: Housefly (Musca domestica)
Percent Mortality
Application Concentration

| Example No. | Compound No. | 0.1 | | 0.05 | | 0.01 | | 0.005 | | 0.001 | |
|---|---|---|---|---|---|---|---|---|---|---|---|
| | | KD | Kill | KD | Kill | KD | Kill | KD | Kill | KD | Kill |
| 307 | 1 | 100 | 100 | 100 | 100 | 0 | 16 | | | | |
| 308 | 2 | 10 | 10 | | | | | | | | |
| 309 | 3 | 0 | 0 | | | | | | | | |
| 310 | 4 | 0 | 12 | | | | | | | | |
| 311 | 5 | 0 | 0 | | | | | | | | |
| 312 | 6 | 100 | 100 | 80 | 100 | 10 | 50 | | | | |
| 313 | 7 | 0 | 12 | | | | | | | | |
| 314 | 8 | 100 | 100 | 100 | 100 | 70 | 80 | 30 | 30 | | |
| 315 | 9 | 72 | 62 | | | | | | | | |
| 316 | 10 | 100 | 100 | 100 | 100 | 94 | 100 | 90 | 88 | 0 | 0 |
| 317 | 11 | 100 | 100 | 30 | 96 | 0 | 0 | | | | |
| 318 | 12 | 80 | 62 | | | | | | | | |
| 319 | 13 | 98 | 86 | | | | | | | | |
| 320 | 14 | 50 | 58 | | | | | | | | |
| 321 | 15 | 0 | 0 | | | | | | | | |
| 322 | 16 | 100 | 100 | 100 | 100 | 40 | 28 | 6 | 0 | | |
| 323 | 17 | 90 | 38 | | | | | | | | |
| 324 | 18 | 100 | 100 | 90 | 86 | 8 | 10 | 0 | 0 | | |
| 325 | 19 | 100 | 100 | 90 | 82 | 0 | 6 | | | | |
| 326 | 20 | 6 | 8 | | | | | | | | |
| 327 | 21 | 0 | 0 | | | | | | | | |
| 328 | 22 | 0 | 0 | | | | | | | | |
| 329 | 23 | 0 | 0 | | | | | | | | |
| 330 | 24 | 0 | 0 | | | | | | | | |
| 331 | 25 | 0 | 0 | | | | | | | | |
| 332 | 26 | 0 | 0 | | | | | | | | |
| 333 | 27 | 0 | 0 | | | | | | | | |
| 334 | 28 | 100 | 100 | 80 | 44 | 0 | 0 | 0 | 0 | | |
| 335 | 29 | 0 | 0 | | | | | | | | |
| 336 | 30 | 0 | 0 | | | | | | | | |
| 337 | 31 | 0 | 0 | | | | | | | | |

TABLE 9-continued

| | | Test Organism: Housefly (Musca domestica) Percent Mortality Application Concentration | | | | | | | | |
|---|---|---|---|---|---|---|---|---|---|---|
| Example No. | Compound No. | 0.1 KD | Kill | 0.05 KD | Kill | 0.01 KD | Kill | 0.005 KD | Kill | 0.001 KD | Kill |
| 338 | 32 | 0 | 0 | | | | | | | | |
| 339 | 33 | 0 | 0 | | | | | | | | |
| 340 | 34 | 0 | 0 | | | | | | | | |
| 341 | 35 | 0 | 0 | | | | | | | | |
| 342 | 36 | 0 | 0 | | | | | | | | |
| 343 | 37 | 0 | 0 | | | | | | | | |
| 344 | 38 | 0 | 0 | | | | | | | | |
| 345 | 39 | 0 | 90 | 0 | 0 | | | | | | |
| 346 | 40 | 100 | 100 | 100 | 100 | 30 | 58 | 0 | 8 | | |
| 347 | 41 | 0 | 0 | | | | | | | | |
| 348 | 42 | 100 | 100 | 100 | 100 | 40 | 40 | 14 | 12 | | |
| 349 | 43 | 0 | 0 | | | | | | | | |
| 350 | 44 | 0 | 0 | | | | | | | | |
| 351 | 45 | 0 | 0 | | | | | | | | |
| 352 | 46 | 0 | 0 | | | | | | | | |
| 353 | 47 | 96 | 100 | 24 | 96 | 0 | 0 | | | | |
| 354 | 48 | | | | | | | | | | |
| 355 | 49 | 30 | 96 | 0 | 0 | | | | | | |
| 356 | 50 | 0 | 0 | | | | | | | | |
| 357 | 51 | 0 | 0 | | | | | | | | |
| 357A | 52 | 20 | 0 | | | | | | | | |
| Untreated | — | 0 | 0 | 0 | 0 | 0 | 0 | 0 | 0 | 0 | 0 |

EXAMPLE 357-B

German Cockroach (*Blatella germanica*)

The procedure for testing against this species was the same as that employed for the housefly, except that twenty specimens were utilized (instead of fifty) and observations were made after 48 hours (instead of 24). In this test, Compound Nos. 9–10, 12–18, 21–22, 24, 29–30, 33, 35–37, 40–46, 48 and 52 were not tested. Compounds 1–8, 11, 19–20, 23, 25, 26–28, 31–32, 34, 38–39, 47, 49–51 were tested at a concentration of 0.1%, with the result that the only activity displayed was by Compound No. 11 which showed a 20% mortality.

EXAMPLES 358–382

Corn Earworm (*Heliothis zea*)

The procedure for testing against this species was the same as that employed for the Southern Armyworm. The Compounds tested were Compound Nos. 1–8, 11, 19–20, 23, 25–28, 31–32, 34, 38–39, 47, 49–51. The results are set forth in Table 10.

TABLE 10

| | | Test Organism: Corn Earworm (Heliothis zea) Percent Mortality Application Concentration | | | |
|---|---|---|---|---|---|
| Example No. | Compound No. | 0.1 | 0.05 | 0.01 | 0.005 |
| 358 | 1 | 100 | 50 | 0 | |
| 359 | 2 | 0 | | | |
| 360 | 3 | 0 | | | |
| 361 | 4 | 0 | | | |
| 362 | 5 | 0 | | | |
| 363 | 6 | 0 | | | |
| 364 | 7 | 0 | | | |
| 365 | 8 | 100 | 20 | 0 | |
| 366 | 11 | 100 | 20 | 0 | |
| 367 | 19 | 30 | | | |
| 368 | 20 | 0 | | | |
| 369 | 23 | 0 | | | |
| 370 | 25 | 60 | | | |
| 371 | 26 | 0 | | | |
| 372 | 27 | 0 | | | |
| 373 | 28 | 100 | 70 | 30 | 0 |
| 374 | 31 | 0 | | | |
| 375 | 32 | 0 | | | |
| 376 | 34 | 0 | | | |
| 377 | 38 | 0 | | | |
| 378 | 39 | 0 | | | |
| 379 | 47 | 0 | | | |
| 380 | 49 | 40 | | | |
| 381 | 50 | 40 | | | |

TABLE 10-continued

| | | Test Organism: Corn Earworm (Heliothis zea) Percent Mortality Application Concentration | | | |
|---|---|---|---|---|---|
| Example No. | Compound No. | 0.1 | 0.05 | 0.01 | 0.005 |
| 382 | 51 | 0 | | | |
| Untreated | — | 0 | 0 | 0 | 0 |

As hereinbefore stated, the oxime carbamates of the present invention are broadly effective as insecticides and acaricides. It should be understood, however, that each particular compound of the present oxime carbamate genus, although exhibiting insecticidal and acaricidal activity as indicated by the foregoing examples, may be not effective against each and every insect and acarid species.

What is claimed is:

1. Novel oxime-carbamates of the formula

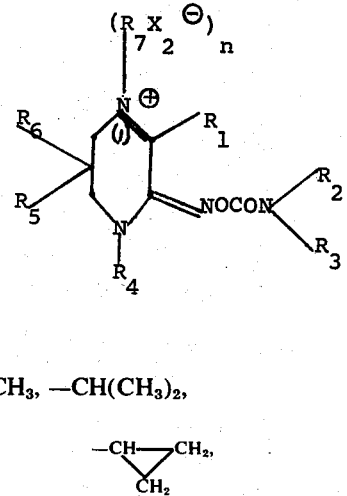

where
$R_1$ is —$CH_3$, —$CH(CH_3)_2$,

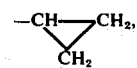

—$C(CH_3)_3$, or —$C_6H_5$;
$R_2$ is —H or —$CH_3$;

R$_3$ is —CH$_3$, —CH$_2$CH$_3$, —(CH$_2$)$_2$CH$_3$, —(CH$_2$)$_3$CH$_3$, —CH$_2$CH$_2$Cl or —C$_6$H$_5$;
R$_4$ is —H, —CH$_3$, —CH$_2$CH$_3$, —(CH$_2$)$_2$CH$_3$, —CH(CH$_3$)$_2$, —(CH$_2$)$_3$CH$_3$, —CH$_2$CH=CH$_2$, —CH$_2$C≡CH, —C$_6$H$_5$,

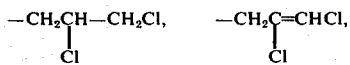

—CH(OH)CCl$_3$, —CH$_2$CH$_2$X$_1$, where X$_1$ is —Cl, —Br, —NH$_2$, —OH, —OCOCH$_3$, —OCOCH$_2$Cl, or —OCONHCH$_3$;

R$_5$ and R$_6$ are each —H or —CH$_3$, with the proviso that when R$_5$ and R$_6$ are both CH$_3$ then both CH$_3$ groups may be on either the same carbon atom or on different carbon atoms;

R$_7$ is H, —CH$_3$ or —CH$_2$C$_6$H$_5$;

X$_2$ is Cl, —Br or —I; and n is 0 or 1, with the proviso that when n is 1 then N bears a ⊕ charge and X$_2$ bears a ⊖ charge.

2. The compound of claim 1 wherein R$_1$ is —CH$_3$, R$_2$ is —H, R$_3$ is —CH$_3$, R$_4$, R$_5$ and R$_6$ are each —H, and n is 0.

3. The compound of claim 1 wherein R$_1$, R$_2$ and R$_3$ are each —CH$_3$, R$_4$, R$_5$ and R$_6$ are each —H, and n is 0.

4. The compound of claim 1 wherein R$_1$ is —CH$_3$, R$_2$ is —H, R$_3$ is —(CH$_2$)$_2$CH$_3$, R$_4$, R$_5$ and R$_6$ are each —H, and n is 0.

5. The compound of claim 1 wherein R$_1$ is —CH$_3$, R$_2$ is —H, R$_3$ is —C$_6$H$_5$, R$_4$, R$_5$ and R$_6$ are each —H, and n is 0.

6. The compound of claim 1 wherein R$_1$ is —CH(CH$_3$)$_2$, R$_2$ is —H, R$_3$ is —CH$_3$, R$_4$, R$_5$ and R$_6$ are each —H, and n is 0.

7. The compound of claim 1 wherein R$_1$ is

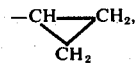

R$_2$ is —H, R$_3$ is —CH$_3$, and R$_4$, R$_5$ and R$_6$ are each —H, and n is 0.

8. The compound of claim 1 wherein R$_1$ is —C$_6$H$_5$, R$_2$ is —H, R$_3$ is —CH$_3$, and R$_4$, R$_5$ and R$_6$ are each —H, and n is 0.

9. The compound of claim 1 wherein R$_1$ is —CH$_3$, R$_2$ is —H, R$_3$ is —CH$_3$, R$_4$ is —H, R$_5$ is —CH$_3$, R$_6$ is —H, and n is 0.

10. The compound of claim 1 wherein R$_1$ is —CH$_3$, R$_2$ is —H, R$_3$ is —CH$_3$, R$_4$ is —H, R$_5$ and R$_6$ are each —CH$_3$, and n is 0.

11. The compound of claim 1 wherein R$_1$ is —CH$_3$, R$_2$ is —H, R$_3$ and R$_4$ are each —CH$_3$, R$_5$ and R$_6$ are each —H, and n is 0.

12. The compound of claim 1 wherein R$_1$ is —CH$_3$, R$_2$ is —H, R$_3$ is —CH$_3$, R$_4$ is —CH$_2$CH$_3$, R$_5$ and R$_6$ are each —H, and n is 0.

13. The compound of claim 1 wherein R$_1$, R$_2$ and R$_3$ are each —CH$_3$, R$_4$ is —CH$_2$CH$_3$, R$_5$ and R$_6$ are each —H, and n is 0.

14. The compound of claim 1 wherein R$_1$ is —CH$_3$, R$_2$ is —H, R$_3$ and R$_4$ are each —CH$_2$CH$_3$, R$_5$ and R$_6$ are each —H, and n is 0.

15. The compound of claim 1 wherein R$_1$ is —CH$_3$, R$_2$ is —H, R$_3$ is —(CH$_2$)$_2$CH$_3$, R$_4$ is —CH$_2$CH$_3$, R$_5$ and R$_6$ are each —H, and n is 0.

16. The compound of claim 1 wherein R$_1$ is —CH$_3$, R$_2$ is —H, R$_3$ is —CH$_2$CH$_2$Cl, R$_4$ is —CH$_2$CH$_3$, R$_5$ and R$_6$ are each —H, and n is 0.

17. The compound of claim 1 wherein R$_1$ is —CH$_3$, R$_2$ is —H, R$_3$ is —CH$_3$, R$_4$ is —(CH$_2$)$_2$CH$_3$, R$_5$ and R$_6$ are each —H, and n is 0.

18. The compound of claim 1 wherein R$_1$ is —CH$_3$, R$_2$ is —H, R$_3$ is —CH$_3$, R$_4$ is —CH(CH$_3$)$_2$, R$_5$ and R$_6$ are each —H, and n is 0.

19. The compound of claim 1 wherein R$_1$ is —CH$_3$, R$_2$ is —H, R$_3$ is —CH$_3$, R$_4$ is —(CH$_2$)$_3$CH$_3$, R$_5$ and R$_6$ are each —H, and n is 0.

20. The compound of claim 1 wherein R$_1$ is —CH$_3$, R$_2$ is —H, R$_3$ is —CH$_3$, R$_4$ is —CH$_2$CH$_2$Cl, R$_5$ and R$_6$ are each —H, and n is 0.

21. The compound of claim 1 wherein R$_1$, R$_2$ and R$_3$ are each —CH$_3$, R$_4$ is —CH$_2$CH$_2$Cl, R$_5$ and R$_6$ are each —H, and n is 0.

22. The compound of claim 1 wherein R$_1$ is —CH$_3$, R$_2$ is —H, R$_3$ is —CH$_2$CH$_3$, R$_4$ is —CH$_2$CH$_2$Cl, R$_5$ and R$_6$ are each —H, and n is 0.

23. The compound of claim 1 wherein R$_1$ is —CH$_3$, R$_2$ is —H, R$_3$ is —(CH$_2$)$_2$CH$_3$, R$_4$ is —CH$_2$CH$_2$Cl, R$_5$ and R$_6$ are each —H, and n is 0.

24. The compound of claim 1 wherein R$_1$ is —CH$_3$, R$_2$ is —H, R$_3$ is —(CH$_2$)$_3$CH$_3$, R$_4$ is —CH$_2$CH$_2$Cl, R$_5$ and R$_6$ are each —H, and n is 0.

25. The compound of claim 1 wherein R$_1$ is —CH$_3$, R$_2$ is —H, R$_3$ and R$_4$ are each —CH$_2$CH$_2$Cl, R$_5$ and R$_6$ are each —H, and n is 0.

26. The compound of claim 1 wherein R$_1$ is —CH(CH$_3$)$_2$, R$_2$ is —H, R$_3$ is —CH$_3$, R$_4$ is CH$_2$CH$_2$Cl, R$_5$ and R$_6$ are each —H, and n is 0.

27. The compound of claim 1 wherein R$_1$ is

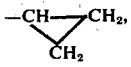

R$_2$ is —H, R$_3$ is —CH$_3$, R$_4$ is —CH$_2$CH$_2$Cl, R$_5$ and R$_6$ are each —H, and n is 0.

28. The compound of claim 1 wherein R$_1$ is —C(CH$_3$)$_3$, R$_2$ is —H, R$_3$ is —CH$_3$, R$_4$ is —CH$_2$CH$_2$Cl, R$_5$ and R$_6$ are each —H, and n is 0.

29. The compound of claim 1 wherein R$_1$ is —CH$_3$, R$_2$ is —H, R$_3$ is —CH$_3$, R$_4$ is —CH$_2$CH$_2$Br, R$_5$ and R$_6$ are each —H, and n is 0.

30. The compound of claim 1 wherein R$_1$, R$_2$ and R$_3$ are each —CH$_3$, R$_4$ is —CH$_2$CH$_2$Br, R$_5$ and R$_6$ are each —H, and n is 0.

31. The compound of claim 1 wherein R$_1$ is —CH$_3$, R$_2$ is —H, R$_3$ is —CH$_3$, R$_4$ is —CH$_2$CH$_2$NH$_2$, R$_5$ and R$_6$ are each —H, and n is 0.

32. The compound of claim 1 wherein R$_1$ is —CH$_3$, R$_2$ is —H, R$_3$ is —CH$_3$, R$_4$ is —CH$_2$CH$_2$OH, R$_5$ and R$_6$ are each —H, and n is 0.

33. The compound of claim 1 wherein R$_1$, R$_2$ and R$_3$ are each —CH$_3$, R$_4$ is —CH$_2$CH$_2$OH, R$_5$ and R$_6$ are each —H, and n is 0.

34. The compound of claim 1 wherein R$_1$ is —CH$_3$, R$_2$ is —H, R$_3$ is —(CH$_2$)$_3$CH$_3$, R$_4$ is —CH$_2$CH$_2$OH, R$_5$ and R$_6$ are each —H, and n is 0.

35. The compound of claim 1 wherein R$_1$ is

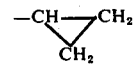

$R_2$ is —H, $R_3$ is —$CH_3$, $R_4$ is —$CH_2CH_2OH$, $R_5$ and $R_6$ are each —H, and $n$ is 0.

36. The compound of claim 1 wherein $R_1$ is —$CH_3$, $R_2$ is —H, $R_3$ is —$CH_3$, $R_4$ is —$CH_2CH_2OCOCH_3$, $R_5$ and $R_6$ are each —H, and $n$ is 0.

37. The compound of claim 1 wherein $R_1$ is —$CH_3$, $R_2$ is H, $R_3$ is —$CH_3$, $R_4$ is —$CH_2CH_2OCOCH_2Cl$, $R_5$ and $R_6$ are each —H, and $n$ is 0.

38. The compound of claim 1 wherein $R_1$ is —$CH_3$, $R_2$ is —H, $R_3$ is —$CH_3$, $R_4$ is —$CH_2CH_2OCONHCH_3$, $R_5$ and $R_6$ are each —H, and $n$ is 0.

39. The compound of claim 1 wherein $R_1$ is —$CH_3$, $R_2$ is —H, $R_3$ is —$CH_3$, $R_4$ is —$CH(OH)CCl_3$, $R_5$ and $R_6$ are each —H, and $n$ is 0.

40. The compound of claim 1 wherein $R_1$, $R_2$ and $R_3$ are each —$CH_3$, $R_4$ is —$CH(OH)CCl_3$, $R_5$ and $R_6$ are each H, and $n$ is 0.

41. The compound of claim 1 wherein $R_1$ is —$CH_3$, $R_2$ is —H, $R_3$ is —$CH_3$, $R_4$ is —$CH_2CH=CH_2$, $R_5$ and $R_6$ are each —H, and $n$ is 0.

42. The compound of claim 1 wherein $R_1$, $R_2$ and $R_3$ are each —$CH_3$, $R_4$ is $CH_2CH=CH_2$, $R_5$ and $R_6$ are each —H, and $n$ is 0.

43. The compound of claim 1 wherein $R_1$ is —$CH_3$, $R_2$ is —H, $R_3$ is —$CH_3$, $R_4$ is —$CH_2C \equiv CH$, $R_5$ and $R_6$ are each —H, and $n$ is 0.

44. The compound of claim 1 wherein $R_1$, $R_2$ and $R_3$ are each —$CH_3$, $R_4$ is —$CH_2C \equiv CH$, $R_5$ and $R_6$ are each —H, and $n$ is 0.

45. The compound of claim 1 wherein $R_1$ is —$CH_3$, $R_2$ is —H, $R_3$ is —$CH_3$, $R_4$ is —$C_6H_5$, $R_5$ and $R_6$ are each —H, and $n$ is 0.

46. The compound of claim 1 wherein $R_1$ is —$CH_3$, $R_2$ is —H, $R_3$ is —$CH_3$, $R_4$ is

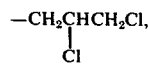

$R_5$ and $R_6$ are each —H, and $n$ is 0.

47. The compound of claim 1 wherein $R_1$ is —$CH_3$, $R_2$ is —H, $R_3$ is —$CH_3$, $R_4$ is

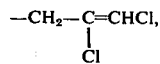

$R_5$ and $R_6$ are each —H, and $n$ is 0.

48. The compound of claim 1 wherein $R_1$ is —$CH_3$, $R_2$ is —H, $R_3$ is —$CH_3$, $R_4$, $R_5$ and $R_6$ are each —H, $R_7$ is —H, $X_2$ is —Cl, and $n$ is 1.

49. The compound of claim 1 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —H, $X_2$ is —Cl, and $n$ is 1.

50. The compound of claim 1 wherein $R_1$ is —$CH_3$, $R_2$ is —H, $R_3$ is —$CH_3$, $R_4$, $R_5$ and $R_6$ are each —H, $R_7$ is —$CH_3$, $X_2$ is —I, and $n$ is 1.

51. The compound of claim 1 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —$CH_3$, $X_2$ is —I, and $n$ is 1.

52. The compound of claim 1 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —$CH_2C_6H_5$, $X_2$ is —Br, and $n$ is 1.

53. The compound of claim 1 wherein $R_1$, $R_2$, and $R_3$ are each —$CH_3$, $R_4$ is —$(CH_2)_2CH_3$, $R_5$ and $R_6$ are each —H, and $n$ is 0.

54. A process for control of insect and acarid infestation which comprises applying either to the locus of said infestation or systemically a pecticidally effective amount of an oxime carbamate of the general formula

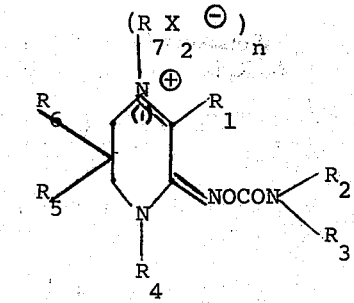

where
$R_1$ is —$CH_3$, —$CH(CH_3)_2$,

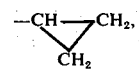

—$C(CH_3)_3$, or —$C_6H_5$;
$R_2$ is —H or —$CH_3$;
$R_3$ is —$CH_3$, —$CH_2CH_3$, —$(CH_2)_2CH_3$, —$(CH_2)_3CH_3$, —$CH_2CH_2Cl$ or —$C_6H_5$,
$R_4$ is —H, —$CH_3$, —$CH_2CH_3$, —$(CH_2)_2CH_3$, —$CH(CH_3)_2$, —$(CH_2)_3CH_3$, —$CH_2CH=CH_2$, —$CH_2C \equiv CH$, —$C_6H_5$,

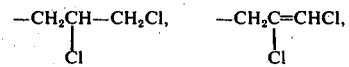

—$CH(OH)CCl_3$, —$CH_2CH_2X_1$, where $X_1$ is —Cl, —Br, —$NH_2$, —OH, —$OCOCH_3$, —$OCOCH_2Cl$, or —O-$CONHCH_3$;
$R_5$ and $R_6$ are each —H or —$CH_3$, with the proviso that when $R_5$ and $R_6$ are both $CH_3$ then both $CH_3$ groups may be on either the same carbon atom or on different carbon atoms;
$R_7$ is H, —$CH_3$ or —$CH_2C_6H_5$
$X_2$ is —Cl, —Br or —I; and
$n$ is 0 or 1, with the proviso that when $n$ is 1 then N bears a $\oplus$ charge and $X_2$ bears a $\ominus$ charge. (1)

55. The process of claim 54 wherein $R_1$ is —$CH_3$, $R_2$ is —H, $R_3$ is —$CH_3$, $R_4$, $R_5$ and $R_6$ are each —H, and $n$ is 0.

56. The process of claim 54 wherein $R_1$, $R_2$ and $R_3$ are each —$CH_3$, $R_4$, $R_5$ and $R_6$ are each —H, and $n$ is 0.

57. The process of claim 54 wherein $R_1$ is —$CH_3$, $R_2$ is —H, $R_3$ is —$(CH_2)_2CH_3$, $R_4$, $R_5$ and $R_6$ are each —H, and $n$ is 0.

58. The process of claim 54 wherein $R_1$ is —$CH_3$, $R_2$ is —H, $R_3$ is —$C_6H_5$, $R_4$, $R_5$ and $R_6$ are each —H, and $n$ is 0.

59. The process of claim 54 wherein $R_1$ is —$CH(CH_3)_2$, $R_2$ is —H, $R_3$ is —$CH_3$, and $R_4$, $R_5$ and $R_6$ are each —H, and $n$ is 0.

60. The process of claim 54 wherein $R_1$ is

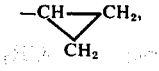

$R_2$ is —H, $R_3$ is —$CH_3$, and $R_4$, $R_5$ and $R_6$ are each —H, and $n$ is 0.

61. The process of claim 54 wherein $R_1$ is —$C_6H_5$, $R_2$ is —H, $R_3$ is —$CH_3$, $R_4$, $R_5$ and $R_6$ are each —H, and $n$ is 0.

62. The process of claim 54 wherein $R_1$ is —$CH_3$, $R_2$ is —H, $R_3$ is —$CH_3$, $R_4$ is —H, $R_5$ is —$CH_3$, $R_6$ is —H, and $n$ is 0.

63. The process of claim 54 wherein $R_1$ is —$CH_3$, $R_2$ is —H, $R_3$ is —$CH_3$, $R_4$ is —H, $R_5$ and $R_6$ are each —$CH_3$, and $n$ is 0.

64. The process of claim 54 wherein $R_1$ is —$CH_3$, $R_2$ is —H, $R_3$ and $R_4$ are each —$CH_3$, $R_5$ and $R_6$ are each —H, and $n$ is 0.

65. The process of claim 54 wherein $R_1$ is —$CH_3$, $R_2$ is —H, $R_3$ is —$CH_3$, $R_4$ is —$CH_2CH_3$, $R_5$ and $R_6$ are each —H, and $n$ is 0.

66. The process of claim 54 wherein $R_1$, $R_2$ and $R_3$ are each —$CH_3$, $R_4$ is —$CH_2CH_3$, $R_5$ and $R_6$ are each —H, and $n$ is 0.

67. The process of claim 54 wherein $R_1$ is —$CH_3$, $R_2$ is —H, $R_3$ and $R_4$ are each —$CH_2CH_3$, $R_5$ and $R_6$ are each —H, and $n$ is 0.

68. The process of claim 54 wherein $R_1$ is —$CH_3$, $R_2$ is —H, $R_3$ is —$(CH_2)_2CH_3$, $R_4$ is —$CH_2CH_3$, $R_5$ and $R_6$ are each —H, and $n$ is 0.

69. The process of claim 54 wherein $R_1$ is —$CH_3$, $R_2$ is —H, $R_3$ is —$CH_2CH_2Cl$, $R_4$ is —$CH_2CH_3$, $R_5$ and $R_6$ are each —H, and $n$ is 0.

70. The process of claim 54 wherein $R_1$ is —$CH_3$, $R_2$ is —H, $R_3$ is —$CH_3$, $R_4$ is —$(CH_2)_2CH_3$, $R_5$ and $R_6$ are each —H, and $n$ is 0.

71. The process of claim 54 wherein $R_1$ is —$CH_3$, $R_2$ is —H, $R_3$ is —$CH_3$, $R_4$ is —$CH(CH_3)_2$, $R_5$ and $R_6$ are each —H, and $n$ is 0.

72. The process of claim 54 wherein $R_1$ is —$CH_3$, $R_2$ is —H, $R_3$ is —$CH_3$, $R_4$ is —$(CH_2)_3CH_3$, $R_5$ and $R_6$ are each —H, and $n$ is 0.

73. The process of claim 54 wherein $R_1$ is —$CH_3$, $R_2$ is —H, $R_3$ is —$CH_3$, $R_4$ is —$CH_2CH_2Cl$, $R_5$ and $R_6$ are each —H, and $n$ is 0.

74. The process of claim 54 wherein $R_1$, $R_2$ and $R_3$ are each —$CH_3$, $R_4$ is —$CH_2CH_2Cl$, $R_5$ and $R_6$ are each H, and $n$ is 0.

75. The process of claim 54 wherein $R_1$ is —$CH_3$, $R_2$ is —H, $R_3$ is —$CH_2CH_3$, $R_4$ is —$CH_2CH_2Cl$, $R_5$ and $R_6$ are each —H, and $n$ is 0.

76. The process of claim 54 wherein $R_1$ is —$CH_3$, $R_2$ is —H, $R_3$ is —$(CH_2)_2CH_3$, $R_4$ is —$CH_2CH_2Cl$, $R_5$ and $R_6$ are each —H, and $n$ is 0.

77. The process of claim 54 wherein $R_1$ is —$CH_3$, $R_2$ is —H, $R_3$ is —$(CH_2)_3CH_3$, $R_4$ is —$CH_2CH_2Cl$, $R_5$ and $R_6$ are each —H, and $n$ is 0.

78. The process of claim 54 wherein $R_1$ is —$CH_3$, $R_2$ is —H, $R_3$ and $R_4$ are each —$CH_2CH_2Cl$, $R_5$ and $R_6$ are each —H, and $n$ is 0.

79. The process of claim 54 wherein $R_1$ is —$CH(CH_3)_2$, $R_2$ is —H, $R_3$ is —$CH_3$, $R_4$ is $CH_2CH\,Cl$, $R_5$ and $R_6$ are each —H, and $n$ is 0.

80. The process of claim 54 wherein $R_1$ is $$-CH\underset{CH_2}{\overset{CH_2}{\diagdown\!\diagup}},$$

$R_2$ is —H, $R_3$ is —$CH_3$, $R_4$ is —$CH_2CH_2Cl$, $R_5$ and $R_6$ are each —H, and $n$ is 0.

81. The process of claim 54 wherein $R_1$ is —$C(CH_3)_3$, $R_2$ is —H, $R_3$ is —$CH_3$, $R_4$ is —$CH_2CH_2Cl$, $R_5$ and $R_6$ are each —H, and $n$ is 0.

82. The process of claim 54 wherein $R_1$ is —$CH_3$, $R_2$ is —H, $R_3$ is —$CH_3$, $R_4$ is —$CH_2CH_2Br$, $R_5$ and $R_6$ are each —H, and $n$ is 0.

83. The process of claim 54 wherein $R_1$, $R_2$ and $R_3$ are each —$CH_3$, $R_4$ is —$CH_2CH_2Br$, $R_5$ and $R_6$ are each —H, and $n$ is 0.

84. The process of claim 54 wherein $R_1$ is —$CH_3$, $R_2$ is —H, $R_3$ is —$CH_3$, $R_4$ is —$CH_2CH_2NH_2$, $R_5$ and $R_6$ are each —H, and $n$ is 0.

85. The process of claim 54 wherein $R_1$ is —$CH_3$, $R_2$ is —H, $R_3$ is —$CH_3$, $R_4$ is —$CH_2CH_2OH$, $R_5$ and $R_6$ are each —H, and $n$ is 0.

86. The process of claim 54 wherein $R_1$, $R_2$ and $R_3$ are each —$CH_3$, $R_4$ is —$CH_2CH_2OH$, $R_5$ and $R_6$ are each —H, and $n$ is 0.

87. The process of claim 54 wherein $R_1$ is —$CH_3$, $R_2$ is —H, $R_3$ is —$(CH_2)_3CH_3$, $R_4$ is —$CH_2CH_2OH$, $R_5$ and $R_6$ are each —H, and $n$ is 0.

88. The process of claim 54 wherein $R_1$ is $$-CH\underset{CH_2}{\overset{CH_2}{\diagdown\!\diagup}}$$

$R_2$ is —H, $R_3$ is —$CH_3$, $R_4$ is —$CH_2CH_2OH$, $R_5$ and $R_6$ are each —H, and $n$ is 0.

89. The process of claim 54 wherein $R_1$ is —$CH_3$, $R_2$ is —H, $R_3$ is —$CH_3$, $R_4$ is —$CH_2CH_2OCOCH_3$, $R_5$ and $R_6$ are each —H, and $n$ is 0.

90. The process of claim 54 wherein $R_1$ is —$CH_3$, $R_2$ is —H, $R_3$ is —$CH_3$, $R_4$ is —$CH_2CH_2OCOCH_2Cl$, $R_5$ and $R_6$ are each —H, and $n$ is 0.

91. The process of claim 54 wherein $R_1$ is —$CH_3$, $R_2$ is —H, $R_3$ is —$CH_3$, $R_4$ is —$CH_2CH_2OCONHCH_3$, $R_5$ and $R_6$ are each —H, and $n$ is 0.

92. The process of claim 54 wherein $R_1$ is —$CH_3$, $R_2$ is —H, $R_3$ is —$CH_3$, $R_4$ is —$CH(OH)CCl_3$, $R_5$ and $R_6$ are each —H, and $n$ is 0.

93. The process of claim 54 wherein $R_1$, $R_2$ and $R_3$ are each —$CH_3$, $R_4$ is —$CH(OH)CCl_3$, $R_5$ and $R_6$ are each H, and $n$ is 0.

94. The process of claim 54 wherein $R_1$ is —$CH_3$, $R_2$ is —H, $R_3$ is —$CH_3$, $R_4$ is —$CH_2CH=CH_2$, $R_5$ and $R_6$ are each —H, and $n$ is 0.

95. The process of claim 54 wherein $R_1$, $R_2$ and $R_3$ are each —$CH_3$, $R_4$ is $CH_2CH=CH_2$, $R_5$ and $R_6$ are each —H, and $n$ is 0.

96. The process of claim 54 wherein $R_1$ is —$CH_3$, $R_2$ is —H, $R_3$ is —$CH_3$, $R_4$ is —$CH_2C\equiv CH$, $R_5$ and $R_6$ are each —H, and $n$ is 0.

97. The process of claim 54 wherein $R_1$, $R_2$ and $R_3$ are each —$CH_3$, $R_4$ is —$CH_2C\equiv CH$, $R_5$ and $R_6$ are each —H, and $n$ is 0.

98. The process of claim 54 wherein $R_1$ is —$CH_3$, $R_2$ is —H, $R_3$ is —$CH_3$, $R_4$ is —$C_6H_5$, $R_5$ and $R_6$ are each —H, and $n$ is 0.

99. The process of claim 54 wherein $R_1$ is —$CH_3$, $R_2$ is —H, $R_3$ is —$CH_3$, $R_4$ is $$-CH_2\underset{Cl}{CH}CH_2Cl,$$

$R_5$ and $R_6$ are each —H, and $n$ is 0.

100. The process of claim 54 wherein $R_1$ is —$CH_3$, $R_2$ is —H, $R_3$ is —$CH_3$, $R_4$ is

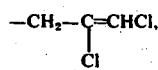

$R_5$ and $R_6$ are each —H, and $n$ is 0.

101. The process of claim 54 wherein $R_1$ is —$CH_3$, $R_2$ is —H, $R_3$ is —$CH_3$, $R_4$, $R_5$ and $R_6$ are each —H, $R_7$ is —H, $X_2$ is —Cl, and $n$ is 1.

102. The process of claim 54 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —H, $X_2$ is —Cl, and $n$ is 1.

103. The process of claim 54 wherein $R_1$ is —$CH_3$, $R_2$ is —H, $R_3$ is —$CH_3$, $R_4$, $R_5$ and $R_6$ are each —H, $R_7$ is —$CH_3$, $X_2$ is —I, and $n$ is 1.

104. The process of claim 54 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —$CH_3$, $X_2$ is —I, and $n$ is 1.

105. The process of claim 54 wherein $R_1$ is —$CH_3$, $R_2$ is —H, $R_3$ is —$CH_3$, $R_4$ is —$CH_2CH_2Cl$, $R_5$ and $R_6$ are each —H, $R_7$ is —$CH_2C_6H_5$, $X_2$ is —Br, and $n$ is 1.

106. The process of claim 54 wherein $R_1$, $R_2$, and $R_3$ are each —$CH_3$, $R_4$ is —$(CH_2)_2CH_3$, $R_5$ and $R_6$ are each —H, and $n$ is 0.

* * * * *

UNITED STATES PATENT OFFICE
CERTIFICATE OF CORRECTION

Patent No. 3,957,990            Dated May 18, 1976

Inventor(s) David L. Booth and Richard M. Rodebaugh

It is certified that error appears in the above-identified patent and that said Letters Patent are hereby corrected as shown below:

In the Abstract — "then N bears a + charge..." should be "then $\underset{(1)}{N}$ bears a + charge...".

Col. 1, line 5 — Should be "oxime-carbamates", not "oxime-carbonates".

Col. 9, line 1 — Should be "$CH_3$", not "$Ch_3$".

Col. 9, line 27 — Should be "then $\underset{(1)}{N}$ bears a ⊕ charge..." not "then N bears a ⊕ charge...".

Table 5, Example 116 — The Percent Mortality for an application concentration of 0.005 should be "30", not "50".

Table 6, Example 204A — Add "40" for The Percent Mortality for an application concentration of 0.00001.

Signed and Sealed this

Seventeenth Day of August 1976

[SEAL]

Attest:

RUTH C. MASON
*Attesting Officer*

C. MARSHALL DANN
*Commissioner of Patents and Trademarks*